US006811560B2

(12) United States Patent
Jones et al.

(10) Patent No.: US 6,811,560 B2
(45) Date of Patent: Nov. 2, 2004

(54) STENT ANEURYSM EMBOLIZATION METHOD AND DEVICE

(75) Inventors: Donald K. Jones, Lauderhill, FL (US); Vladimir Mitelberg, Aventura, FL (US)

(73) Assignee: Cordis Neurovascular, Inc., Miami Lakes, FL (US)

( * ) Notice: Subject to any disclaimer, the term of this patent is extended or adjusted under 35 U.S.C. 154(b) by 121 days.

(21) Appl. No.: 09/957,183

(22) Filed: Sep. 20, 2001

(65) Prior Publication Data

US 2003/0055451 A1 Mar. 20, 2003

(51) Int. Cl.[7] .............................................. A61M 29/00
(52) U.S. Cl. ..................................................... 606/200
(58) Field of Search ............................... 623/1.11, 1.22, 623/1.15; 606/151, 157, 158, 191, 192, 194, 195, 198, 200, 213, 215

(56) References Cited

U.S. PATENT DOCUMENTS

| | | | |
|---|---|---|---|
| 4,512,338 A | | 4/1985 | Balko et al. |
| 4,994,069 A | | 2/1991 | Ritchart et al. |
| 5,411,550 A | * | 5/1995 | Herweck et al. ............ 623/1.27 |
| 5,527,338 A | | 6/1996 | Purdy |
| 5,693,067 A | | 12/1997 | Purdy |
| 5,749,894 A | * | 5/1998 | Engelson ..................... 606/191 |
| 5,766,219 A | | 6/1998 | Horton |
| 5,891,192 A | * | 4/1999 | Murayama et al. ......... 623/1.48 |
| 5,935,148 A | * | 8/1999 | Villar et al. ................. 606/213 |
| 5,951,599 A | * | 9/1999 | McCrory ..................... 623/1.1 |
| 5,980,514 A | * | 11/1999 | Kupiecki et al. ............ 606/194 |
| 6,036,720 A | * | 3/2000 | Abrams et al. .............. 606/200 |
| 6,063,070 A | * | 5/2000 | Eder ............................ 606/213 |
| 6,063,104 A | * | 5/2000 | Villar et al. ................. 606/213 |
| 6,063,111 A | * | 5/2000 | Hieshima et al. ........... 623/1.22 |
| 6,086,577 A | * | 7/2000 | Ken et al. .................... 606/200 |
| 6,093,199 A | * | 7/2000 | Brown et al. ................ 606/200 |
| 6,168,592 B1 | | 1/2001 | Kupiecki et al. |
| 6,193,708 B1 | * | 2/2001 | Ken et al. .................... 606/194 |
| 6,346,117 B1 | * | 2/2002 | Greenhalgh ................. 606/200 |
| 6,361,558 B1 | * | 3/2002 | Hieshima et al. ........... 623/1.16 |
| 6,383,174 B1 | * | 5/2002 | Eder ............................ 623/1.1 |
| 6,454,780 B1 | * | 9/2002 | Wallace ....................... 606/151 |

FOREIGN PATENT DOCUMENTS

| | | |
|---|---|---|
| EP | 1129666 A1 | 9/2001 |
| WO | WO 98/02100 A1 | 1/1998 |
| WO | WO 99/05977 A1 | 2/1999 |
| WO | WO 00/07524 A1 | 2/2000 |

OTHER PUBLICATIONS

European Search Report EP 02 25 6399 dated Nov. 7, 2002.

* cited by examiner

Primary Examiner—David O. Reip
Assistant Examiner—Jessica R. Baxter

(57) ABSTRACT

A method and device used for treating an aneurysm of a patient. An embolization element that is adapted to reduce or block the blood flow into the aneurysm, together with a stent connected to the embolization element, is provided. The embolization element includes an expandible member. The embolization element and the stent are introduced into the vessel leading to and communicating with the aneurysm. The embolization element is directed into the aneurysm, with the stent being located in the vessel communicating with the aneurysm. In this manner, the stent becomes compressed against the inner wall of the vessel for anchoring the embolization element. In one form of the invention, the stent comprises a helical coil and the embolization element comprises a collapsible framework.

30 Claims, 2 Drawing Sheets

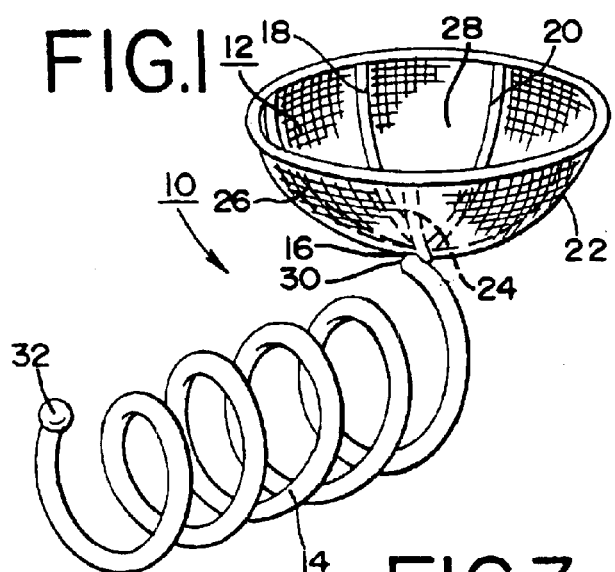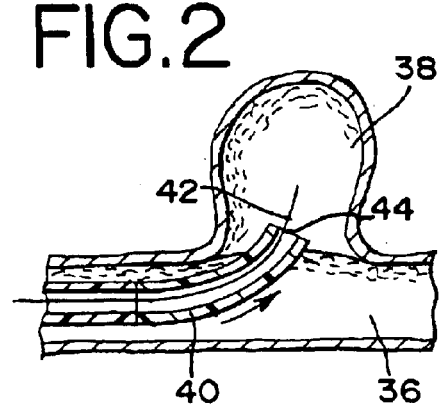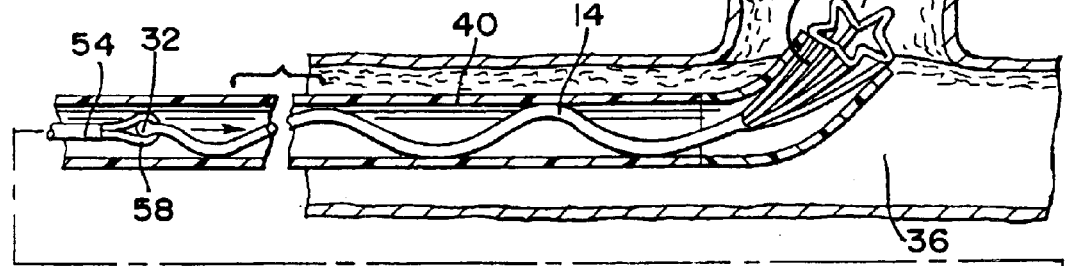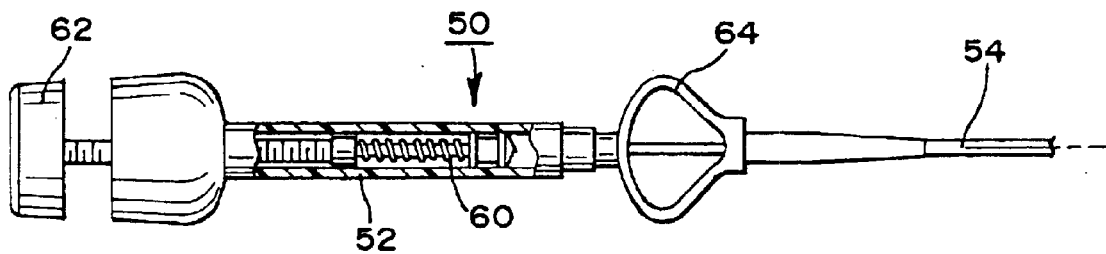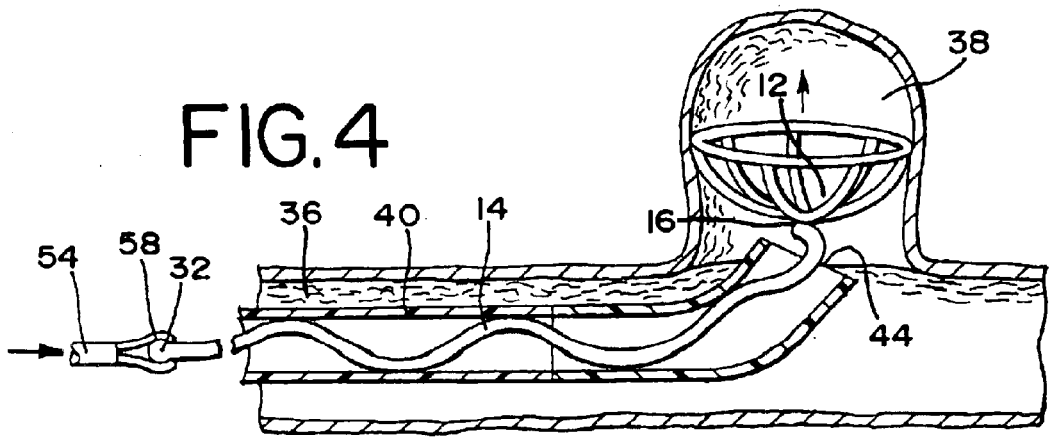

US 6,811,560 B2

1

STENT ANEURYSM EMBOLIZATION METHOD AND DEVICE

FIELD OF THE INVENTION

The present invention concerns a novel method and device for treating an aneurysm of a patient and, more particularly, a method and device in which an embolic device is maintained within the aneurysm.

BACKGROUND OF THE INVENTION

A well-known method of treating an aneurysm of a vessel wall includes the placement of a number of embolic coils within the aneurysm. Typically, a deployment device is used to introduce the coils, one by one, via a microcatheter, into the aneurysm. In wider neck aneurysms, it has been found that the embolic coils tend to migrate back to the parent vessel, which may result in occlusion of the parent vessel. Further, migration of the coil or coils back into the parent vessel may cause the coil or coils to be moved by the blood into another portion of the vessel, creating potentially serious problems.

It is, therefore, an object of the present invention to provide a method for maintaining an embolic device within an aneurysm.

Another object of the present invention is to provide a method that is relatively simple in operation for treating an aneurysm.

A still further object of the present invention is to provide a method for treating an aneurysm of a patient in which migration of the embolic device back into the parent vessel wall is prevented.

Another object of the present invention is to provide a vaso-occlusive device in which an embolization element is anchored within a patient's aneurysm.

Other objects and advantages of the present invention will become apparent as the description proceeds.

SUMMARY OF THE INVENTION

In accordance with the present invention, a method is provided for treating an aneurysm of a patient. The method comprises the steps of introducing into the patient's aneurysm an embolization element that is adapted to reduce or block the blood flow into the aneurysm. The embolization element includes an expandable member. A stent is introduced into a vessel leading to and communicating with the aneurysm, with the stent becoming compressed against the inner wall of the vessel for anchoring the embolization element.

In the illustrative embodiment of the invention, the embolization element comprises a collapsible framework supporting a mesh or membrane. The mesh or membrane comprises a biocompatible material from the group consisting of PVA, PVP and collagen. The embolization element is generally cup-shaped and has a cross sectional area that, when introduced into the aneurysm, reduces or restricts blood flow into the aneurysm.

In the illustrative embodiment, the helical member comprises a coil having an enlarged proximal end and an enlarged distal end. The coil further comprises a radiopaque coil overlying a core wire with the enlarged ends restricting the movement of the core wire relative to the radiopaque coil.

In the illustrative embodiment of the invention, the introducing steps include the steps of providing a deployment

2 device for carrying and delivering the embolization element. The deployment device and the embolization element are introduced into the vessel of the patient via a microcatheter. The embolization element is positioned in a desired location in the aneurysm and is released from the deployment device. In the illustrative embodiment, the embolization element and the helical member are introduced simultaneously.

A more detailed explanation of the invention is provided in the following description and claims, and is illustrated in the accompanying drawings.

BRIEF DESCRIPTION OF THE DRAWINGS

FIG. 1 is a perspective view of a vaso-occlusive device that can be used in accordance with the principles of the present invention;

FIG. 2 is a diagrammatic view of the introduction of a microcatheter;

FIG. 3 is a diagrammatic view of the introduction of a embolization element in accordance with the principles of the present invention;

FIG. 4 is a diagrammatic view, similar to a portion of FIG. 3, showing the embolization device that is expanded;

DETAILED DESCRIPTION OF THE ILLUSTRATIVE EMBODIMENT

Figure 5:
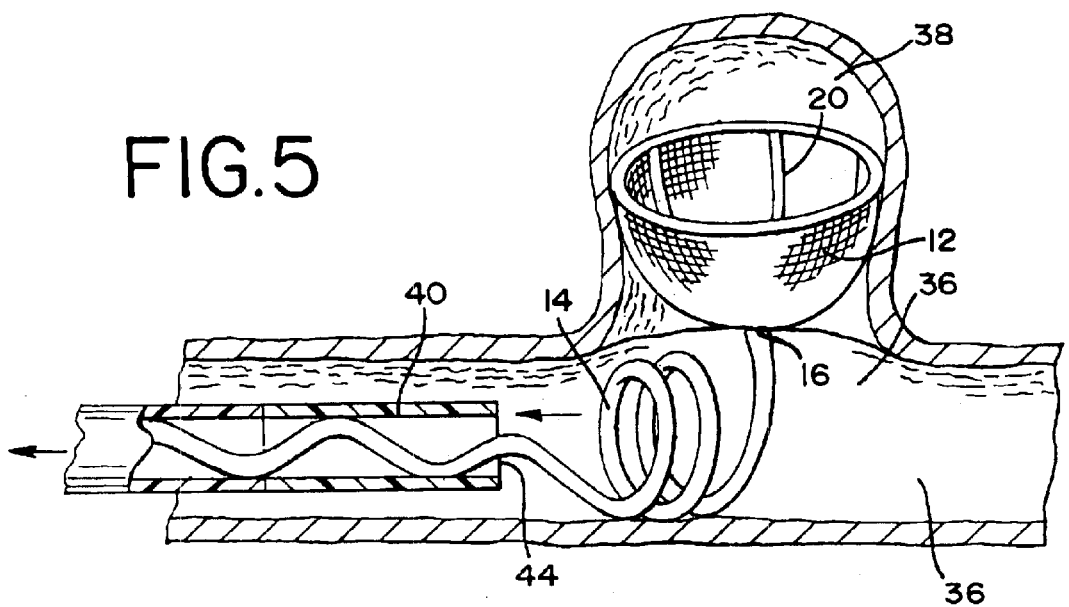
FIG. 5 is a diagrammatic view, similar to FIG. 4, but showing the device as the microcatheter is being withdrawn.

Referring to FIG. 1, a vaso-occlusive device 10 is illustrated therein including an embolization element 12 and a stent 14 connected at the base 16 of embolization element 12. The embolization element includes a collapsible framework in 18, 20, 22, 24 and 26, with an attached mesh or membrane 28 for reducing or blocking blood flow into an aneurysm. Stent 14 is formed of a flexible wire that has been shaped into a cylindrical helix with its distal end 30 attached to the base 16 of embolization element 12.

In the illustrative embodiment, the stent 14 is formed of a superelastic material in wire or tube form that will form and retain the helical configuration of the stent. A platinum coil is placed over the core to provide radiopacity and aid in the delivery of the device. The core wire is enlarged at the proximal end 32 and the distal end 30, to fill the lumen of the coil. This provides a method of restricting the movement of the core wire relative to the platinum coil. The ends of the core are then made atraumatic by beading or the like, as illustrated in FIG. 1. The assembly is then shaped using a die at a temperature and time sufficient for the assembly to retain the desired configuration. The shaped assembly is then placed in a fixture so that the aneurysm embolization element 12 can be attached.

Mesh or membrane 28 of the embolization element 12 may be formed of biocompatible substances such as PVA, PVP or collagen. The stent may be attached to the base 16 of the embolization element 12 by placing the embolization element on the distal end of stent 30 and applying a small amount of UV curable adhesive to secure the embolization element 12 to the stent 14.

A method of treating an aneurysm of a patient in accordance with the present invention is illustrated in FIGS. 2–8. Referring to FIG. 2, parent vessel 36 contiguous with aneurysm 38 is illustrated. As is known in the art with respect to treating an aneurysm, a microcatheter with guidewire 42 are introduced into the patient's vascular system so that the microcatheter, following the guidewire 42, is positioned with its distal end 44 being located at the mouth of the aneurysm. Guidewire 42 is withdrawn and vaso-occlusive device 10 is introduced as follows. Vaso-occlusive device 10 is inserted into the proximal end of microcatheter 40, with the embolization element 12 being in a collapsed or folded condition so that it fits within the microcatheter. As illustrated in FIG. 3, a deployment device 50 is used for placing the vaso-occlusive device in the desired location. Although no limitation is intended, one example of a deployment device that can be used in connection with the present invention is disclosed in Hieshima U.S. Pat. No. 6,113,622, the disclosure of which is incorporated herein by reference. Deployment device 50 includes a hydraulic injector or syringe 52, coupled to the proximal end of a catheter 54. Bead 32 at the proximal end of stent 14 is disposed within the lumen of the distal end 58 of catheter 54. Bead 32 is tightly held within the lumen of distal section 58 until the deployment system is activated for release of a stent.

Syringe 52 includes a threaded piston 60 which is controlled by a handle 62. Catheter 54 includes a wing hub 64 which aids in the insertion of a catheter 54 into microcatheter 40.

Figure 6:
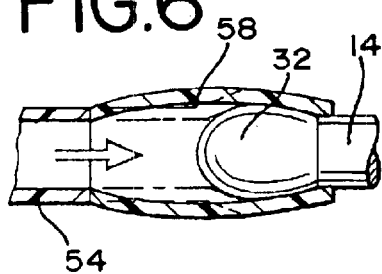
FIG. 6 is an enlarged cross-sectional view, partially broken, of the deployment device connection to the vaso-occlusive device.
Figure 7:
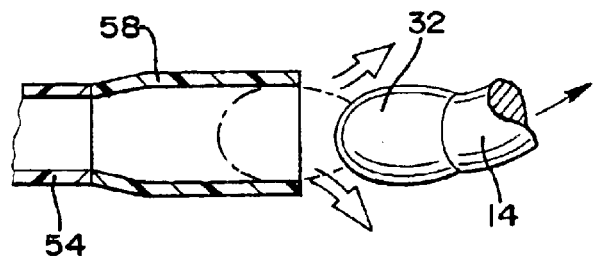
FIG. 7 is a view, similar to FIG. 6, but after the deployment device has been disengaged from the vaso-occlusive device.

As illustrated in FIG. 6, the distal end 58 is flexible, as disclosed in Hieshima U.S. Pat. No. 6,113,622, and tightly engages bead 32 of stent 14. However when handle 62 is activated to move the piston forward as illustrated in FIG. 7, distal end 58 will expand by this hydraulic operation to release bead 32 and the stent and embolic device to which it is connected.

Figure 8:
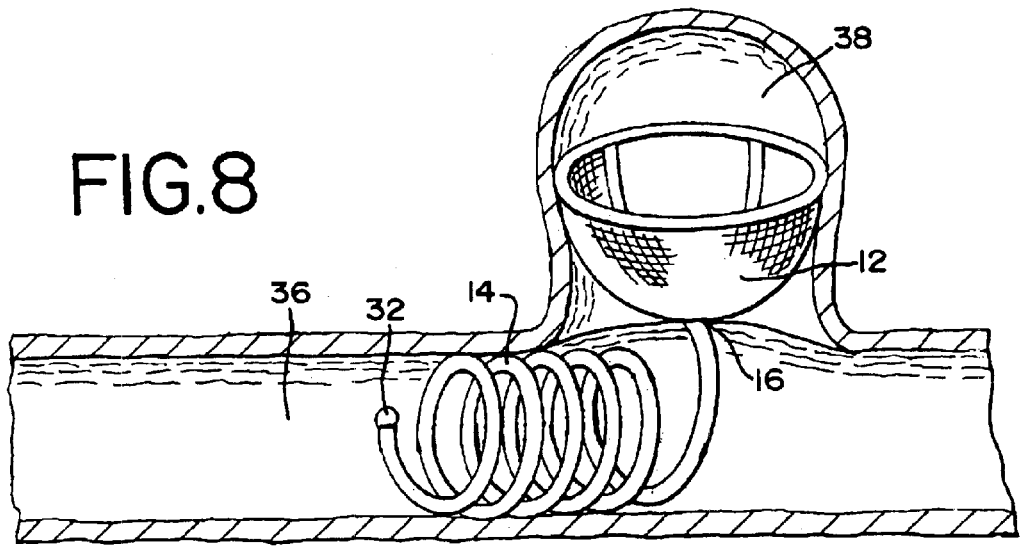
FIG. 8 is a diagrammatic view of the vaso-occlusive device of FIG. 1 in place within an aneurysm.

Now referring back to FIG. 4, it can be seen that vaso-occlusive device 10 has been moved forwardly through microcatheter 40 so that embolization element 12 is located within aneurysm 38 and the framework of embolization element 12 has expanded to form a cup shaped element which substantially engages the inner walls of the aneurysm to substantially block blood flow into the aneurysm. Once the vaso-occlusive device is positioned as illustrated in FIG. 4, handle 62 is activated to release bead 32 from deployment device 50 and, as illustrated in FIG. 5, microcatheter 4 is withdrawn. As microcatheter 40 is withdrawn, the wire forming stent 14 will become released and spring into its coiled form, as illustrated in FIG. 8. FIG. 8 shows the vaso-occlusive device 12 fully delivered to the aneurysm with the stent 14 providing a radial force on the vessel to prevent movement and migration on the aneurysm embolization element 12. As illustrated in FIG. 8, the outer diameter of the helical coil which forms stent 14 engages the inner wall of the parent vessel.

By utilizing stent 14 with aneurysm embolization element 12, there is an improvement over a coil or stent alone in that the stent can provide more radial force on the vessel to prevent movement and migration of the aneurysm embolization element. This removes the necessity of requiring the aneurysm embolization element to provide the radial force, which would cause difficulty in delivering the device through the small lumen of a microcatheter and would also result in an excessive pressure on the aneurysm wall. Further, with the method and device of the present invention, the treatment of aneurysms requires deployment of only one device and one treatment as opposed to multiple coils and possible multiple treatments.

The method of stent construction provides a method of stretch resistance without physically attaching the core wire to the proximal and distal ends of the coil. As the coil begins to stretch, it cinches on the head of the core wire and prevents further stretching.

The aneurysm embolization element 12 provides a scaffolding on which tissue can grow, providing a treatment that is more efficacious then current treatments. The mesh or membrane 12 can carry a chemotherapeutic agent or may carry genetically engineered substances (cells/viral vectors). Embolization element 12 may be made radiopaque using fillers or chemically attached radiopaque substances such as iodine.

Although stent 14 is illustrated in the form of a helical coil, other equivalent shapes may be operable to prevent movement and migration of the aneurysm embolization element. Further, although the embolization element 12 is shown with a generally cup shaped configuration, other equivalent configurations that are suitable for reducing or blocking flow into the aneurysm may be utilized. Although the deployment device 50 is illustrated as hydraulic, the detachment system can use other equivalent methods such as electrolytic, thermoadhesive or mechanical. Depending on the type of detachment the proximal end of the stent can be configured to couple as desired to the pusher.

Although an illustrative embodiment of the invention has been shown and described, it is to be understood that various other modifications and substitutions may be made by those skilled in the art without departing from the novel spirit and scope of the present invention.

What is claimed is:

1. A method for treating an aneurysm of a patient, the aneurysm being separated from a vessel of the patient by a mouth that is contiguous with and communicates with the vessel and the aneurysm, comprising the steps of:
   providing an embolization element that is adapted to be positioned within the aneurysm to reduce or block the blood flow into the aneurysm, with a stent connected to the embolization element, the embolization element including an expandable member;
   introducing the embolization element and the stent into the vessel leading to and communicating with the aneurysm;
   directing the embolization element through said mouth into the aneurysm with the stent being located in the vessel communicating with the aneurysm whereby the stent becomes expanded against the inner wall of the vessel for anchoring the embolization element.

2. A method as defined in claim 1, in which the stent comprises a helical coil.

3. A method as defined in claim 1, in which the embolization element comprises a collapsible framework.

4. A method as defined in claim 3, in which the collapsible framework supports a mesh or membrane.

5. A method as defined in claim 4, in which the mesh or membrane comprises a biocompatible material from the group consisting of PVA, PVP and collagen.

6. A method as defined in claim 1, in which the embolization element is generally cup-shaped.

7. A method as defined in claim 4, in which the mesh or membrane has a cross-sectional area that, when introduced into the aneurysm, reduces or restricts blood flow into the aneurysm.

8. A method as defined in claim 2, in which the helical member comprises a coil having an enlarged proximal end and an enlarged distal end.

9. A method as defined in claim 8, in which the coil further comprises a radiopaque coil overlying a core wire with said enlarged ends restricting the movement of the core wire relative to the radiopaque coil.

10. A method as defined in claim 2, in which the helical coil has atraumatic ends.

11. A method as defined in claim 1, wherein the introducing step includes the steps of providing a deployment device for carrying and delivering the embolization element and introducing the deployment device and the embolization element into the vessel of the patient via a catheter.

12. A method as defined in claim 11, wherein the directing step includes the steps of positioning the embolization element in a desired location in the aneurysm;
    releasing the embolization element from the deployment device;
    withdrawing the catheter from the patient's vessel; and
    withdrawing the deployment device from the patient's vessel.

13. A method as defined in claim 1, in which the distal end of the stent is fastened to a proximal end of the embolization element.

14. A method for treating an aneurysm of a patient, the aneurysm being separated from a vessel of the patient by a mouth that is contiguous with and communicates with the vessel and the aneurysm, comprising the steps of:
    providing an embolization element that is adapted to be positioned within the aneurysm to reduce or block the blood flow into the aneurysm, with a stent connected to the embolization element, the embolization element including an expandable member;
    introducing the embolization element and the stent into the vessel leading to and communicating with the aneurysm;
    providing a deployment device for carrying and delivering the embolization element and the stent simultaneously;
    introducing the deployment device with the embolization element and stent into the vessel of the patient via a catheter;
    directing the embolization element through said mouth into the aneurysm with the stent being located in the vessel communicating with the aneurysm;
    releasing the embolization element and the helical member from the deployment device; and
    withdrawing the catheter from the patient's vessel whereby the stent becomes expanded against the inner wall of the vessel.

15. A method as defined in claim 14, in which the stent comprises a helical coil.

16. A method as defined in claim 14, in which the embolization element comprises a collapsible framework.

17. A method as defined in claim 16, in which the collapsible framework supports a mesh or membrane.

18. A method as defined in claim 14, in which the embolization element is generally cup shaped.

19. A method as defined in claim 14, in which the mesh or membrane has a cross sectional area that, when introduced into the aneurysm, reduces or restricts blood flow to the aneurysm.

20. The method of claim 14 in which, after said release, the stent expands to be compressed against the inner wall of the vessel to a degree sufficient to prevent movement and migration of the stent and aneurysm embolization element, to avoid any excessive pressure on the aneurysm wall by the embolization element.

21. A medical device for treating an aneurysm of a patient, the aneurysm being separated from a vessel of the patient by a mouth that is contiguous with and communicates with the vessel and the aneurysm, which comprises:
    an embolization element comprising a collapsible framework supporting a mesh or membrane which, when expanded, forms a generally cup-shape;
    said embolization element being adapted to be positioned within the aneurysm to reduce or block the blood flow into the aneurysm;
    a helical member having a proximal end and a distal end, said distal end being connected to a proximal end of said generally cup-shaped embolization element;
    said helical member being adapted for positioning within a catheter in a nonexpanded configuration and, when released from said catheter, being adapted to expand radially to expand against the inner wall of a vessel leading to the patient's aneurysm for anchoring the embolization element when the embolization element is directed through said mouth and positioned within the aneurysm.

22. A medical device as defined in claim 21, in which the helical member comprises a coil having an enlarged proximal end and an enlarged distal end.

23. A medical device as defined in claim 22, in which said coil further comprises a radiopaque coil overlying a core wire with said enlarged ends restricting the movement of the core wire relative to the radiopaque coil.

24. A medical device as defined in claim 21, in which the helical member has atraumatic ends.

25. A medical device as defined in claim 21, in which the mesh or membrane comprises a biocompatible material from the group consisting of PVA, PVP and collagen.

26. A medical device as defined in claim 21, in which the embolization element carries a chemotherapeutic agent.

27. A medical device as defined in claim 21, in which the embolization element carries genetically engineered substances.

28. A medical device as defined in claim 21, in which the embolization element is radiopaque.

29. The medical device of claim 21, in which said helical member expands radially to a sufficient degree that compression against the inner wall prevents movement and migration of the aneurysm embolization element while avoiding excessive pressure on the wall of the aneurysm.

30. A method for treating an aneurysm of a patient, the aneurysm being separated from a vessel of the patient by a mouth that is contiguous with and communicates with the vessel of the aneurysm comprising the steps of:
    providing an embolization element that is adapted to reduce or block the blood flow into the aneurysm, with a stent connected to the embolization element, the embolization element including an expandable member;
    said embolization element being adapted to be positioned within the aneurysm to reduce or block the blood flow into the aneurysm;
    introducing the embolization element and the stent into the vessel leading to and communicating with the aneurysm;
    directing the embolization element through said mouth into the aneurysm with the stent being located in the vessel communicating with the aneurysm whereby the stent becomes expanded against the inner wall of the vessel for anchoring the embolization element to a degree sufficient to prevent movement and migration of the aneurysm embolization element, to avoid any excessive pressure on the aneurysm wall by the embolization element.

* * * * *